(12) United States Patent
Damazo et al.

(10) Patent No.: US 10,620,179 B2
(45) Date of Patent: *Apr. 14, 2020

(54) SYSTEMS AND METHODS FOR NON-FLAMMABLE INDICATION OF INCENDIVITY

(71) Applicant: The Boeing Company, Chicago, IL (US)

(72) Inventors: Jason Scott Damazo, Seattle, WA (US); Eddie Kwon, Seattle, WA (US); Andrew Michael Robb, Everett, WA (US)

(73) Assignee: The Boeing Company, Chicago, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/181,060

(22) Filed: Nov. 5, 2018

(65) Prior Publication Data

US 2019/0072535 A1 Mar. 7, 2019

Related U.S. Application Data

(63) Continuation of application No. 15/214,214, filed on Jul. 19, 2016, now Pat. No. 10,145,834.

(51) Int. Cl.
*G01N 33/22* (2006.01)
*G01N 31/12* (2006.01)
(Continued)

(52) U.S. Cl.
CPC ............. *G01N 33/22* (2013.01); *G01N 25/52* (2013.01); *G01N 25/46* (2013.01); *G01N 31/12* (2013.01);
(Continued)

(58) Field of Classification Search
CPC ...... G01N 33/22; G01N 33/227; G01N 25/22; G01N 25/36; G01N 25/46; G01N 25/48;
(Continued)

(56) References Cited

U.S. PATENT DOCUMENTS 3,999,936 A 12/1976 Hasselmann
4,115,235 A 9/1978 Capone
(Continued)

OTHER PUBLICATIONS

Schmidt et al., "Dielectric Permittivity of Eight Gases Measured with Cross Capacitors," International Journal of Thermoplastics, vol. 24, No. 2, Mar. 2003.
(Continued)

*Primary Examiner* — Maureen Wallenhorst
(74) *Attorney, Agent, or Firm* — Dascenzo Intellectual Property Law, P.C.

(57) ABSTRACT

Incendivity test systems and methods are disclosed. Incendivity test systems include a non-flammable gas mixture and a test article. The non-flammable gas mixture includes a thermally reactive reagent that is formulated to thermally react to produce a reaction product. Incendivity test systems also include an energy source configured to apply an energy discharge such as a simulated lightning strike to the test article. Incendivity test systems also include a detection device configured to measure an indicator species in the non-flammable gas mixture (e.g., the thermally reactive reagent and/or the reaction product). Incendivity test methods include contacting the test article with the non-flammable gas mixture, applying the energy discharge to the test article, and then measuring the amount of the indicator species and determining the incendivity of the test article in response to the energy discharge based upon the amount of the indicator species.

27 Claims, 2 Drawing Sheets

(51) Int. Cl.
*G01N 25/46* (2006.01)
*G01N 25/52* (2006.01)

(52) U.S. Cl.
CPC .... *Y10T 436/196666* (2015.01); *Y10T 436/24* (2015.01)

(58) Field of Classification Search
CPC ............... G01N 31/12; Y10T 436/19; Y10T 436/196666; Y10T 436/209163; Y10T 436/24; Y10T 436/25875
USPC ....... 436/124, 126, 127, 135, 137, 147, 155, 436/156, 160, 161, 164, 171, 172, 173, 436/181; 422/78, 80, 82.05, 82.08, 82.09, 422/83, 89, 94
See application file for complete search history.

(56) References Cited

U.S. PATENT DOCUMENTS

| | | | |
|---|---|---|---|
| 4,348,888 A | 9/1982 | Snee | |
| 5,053,200 A | 10/1991 | Schaeffer et al. | |
| 10,145,834 B2 * | 12/2018 | Damazo | G01N 33/22 |
| 2014/0331743 A1 | 11/2014 | Kwon et al. | |
| 2016/0047719 A1 | 2/2016 | Kwon et al. | |
| 2016/0123860 A1 | 5/2016 | McBrien et al. | |
| 2018/0024105 A1 | 1/2018 | Damazo et al. | |
| 2018/0074036 A1 | 3/2018 | Boettcher et al. | |

OTHER PUBLICATIONS

Section 7.7 of Aircraft Lightning Test Methods, SAE International, ARP5416A, pp. 99-105, Feb. 28, 2014.
Shepard et al., "*Spark Ignition Energy Measurements in Jet A*," Explosion Dynamics Laboratory Report FM97-9, Graduate Aeronautical Laboratories, California Institute of Technology, May 3, 1999, revised Jan. 24, 2000.
Jaeger et al., "*Prevent Explosions of Combustible Dusts*," Chemical Engineering Progress, Jun. 1999.
Crouch, "*Aircraft Fuel System Lightning Protection Design and Qualification Test Procedures Development*," Technical Report, DOT/FAA/CT-94/74, Sep. 1994.
Buhler et al., "*Test methodology to evaluate the safety of materials using spark incendivity*," Journal of Electrotatics, vol. 64, pp. 744-751, 2006.

* cited by examiner

SYSTEMS AND METHODS FOR NON-FLAMMABLE INDICATION OF INCENDIVITY

RELATED APPLICATIONS

This application claims priority to U.S. patent application Ser. No. 15/214,214, entitled "SYSTEMS AND METHODS FOR NON-FLAMMABLE INDICATION OF INCENDIVITY," now U.S. Pat. No. 10,145,834, filed on Jul. 19, 2016, the complete disclosure of which is hereby incorporated by reference.

FIELD

The present disclosure relates to systems and methods for non-flammable indication of incendivity.

BACKGROUND

In many situations, apparatuses must operate in potentially hazardous conditions, such as where a fuel mixture may be ignited by uncontrolled operating or environmental conditions. For example, vehicles, including aerospace vehicles, typically operate with a fuel that must be maintained in a safe condition during storage and use. The ignition hazard should be minimized even when the vehicle is subject to uncontrolled events such as an accident, electrical malfunction, a lightning strike, or static electrical discharge. Other applications requiring ignition hazard consideration include fuel transport, fuel storage, mining operations, chemical processing, metal fabrication, power plant construction and operation, and operations which involve combustible particulate such as sawdust, metal, flour, and grain.

Design of apparatuses exposed to ignition hazards typically involves reducing the likelihood of ignition, containing the ignition hazard, and/or withstanding the ignition hazard. Test systems may facilitate or verify the design of a component by simulating or applying ignition hazard precursors such as heating, a simulated lightning strike, or other electromagnetic effects (e.g., arcing, electrostatic discharge, heating, and/or hot particle ejection).

In the aerospace industry, the Federal Aviation Administration (FAA) requires ignition source tests for components potentially exposed to fuel-vapor environments (specified in SAE ARP 5416A (SAE Aerospace)). One test method is the photographic method and another method is the ignitable mixture (flammable gas) test method. The photographic method subjects a test article to an ignition hazard precursor (e.g., simulated lightning strike) in a darkened chamber to observe the light produced by arcs (if any) emitted by the test article. The photographic method is suitable for arcs, which are relatively quick and bright, but not well suited for hot particles, other heat sources, or ignition hazards that impart energy more slowly or which do not have corresponding light emission.

The ignitable mixture (flammable gas) test method subjects the test article to the ignition hazard precursor in a flammable atmosphere within a combustion chamber (which may be referred to as a combustion vessel or a bomb). If the test article produces an ignition hazard, the flammable atmosphere explosively ignites in the combustion chamber. The contained explosion may be detected by various techniques (e.g., by detecting the pressure change, the light, the heat, and/or the sound of the explosion). The ignitable mixture test method has the advantage of being more realistic than the photographic method, in that the flammable atmosphere reacts in the same manner (thermal reaction) as does the atmosphere that may contact the test article in actual use. The primary disadvantage of the ignitable mixture test method is the use of the flammable atmosphere, which requires care in the preparation and fabrication of the combustion chamber, and care in handling the flammable gas. Some test articles may be quite large (e.g., components or the entirety of a wing fuel tank of an aircraft) and have consequent greater demands for the safe operation of the combustion chamber and the safe handling of the flammable atmosphere. Additionally, because an ignition hazard causes the flammable atmosphere to be consumed, the ignitable mixture (flammable gas) test method produces merely a pass-fail result.

SUMMARY

Incendivity test systems and methods are disclosed. Incendivity test systems include a non-flammable gas mixture and a test article. The non-flammable gas mixture is non-flammable yet includes a thermally reactive reagent that is formulated to thermally react to produce a reaction product without self-propagating combustion or explosion. For example, the non-flammable gas mixture may be a mixture below the lower flammability limit of the thermally reactive reagent. Incendivity test systems also include an energy source configured to apply an energy discharge such as a simulated lightning strike to the test article. Incendivity test systems also include a detection device configured to measure an indicator species in the non-flammable gas mixture (e.g., the thermally reactive reagent and/or the reaction product).

Incendivity test methods include contacting a test article with a non-flammable gas mixture that includes a thermally reactive reagent. Incendivity test methods include applying an energy discharge to the test article while the test article is in contact with the non-flammable gas mixture. After applying the energy discharge, incendivity test methods include measuring an amount of one or more components of the non-flammable gas mixture (i.e., one or more indicator species) that represents an amount of the thermally reactive reagent that reacted in response to applying the energy discharge. Incendivity test methods also include determining an incendivity of the test article in response to the energy discharge based upon the amount of the thermally reactive reagent that reacted in response to applying the energy discharge.

DESCRIPTION

Figure 1:
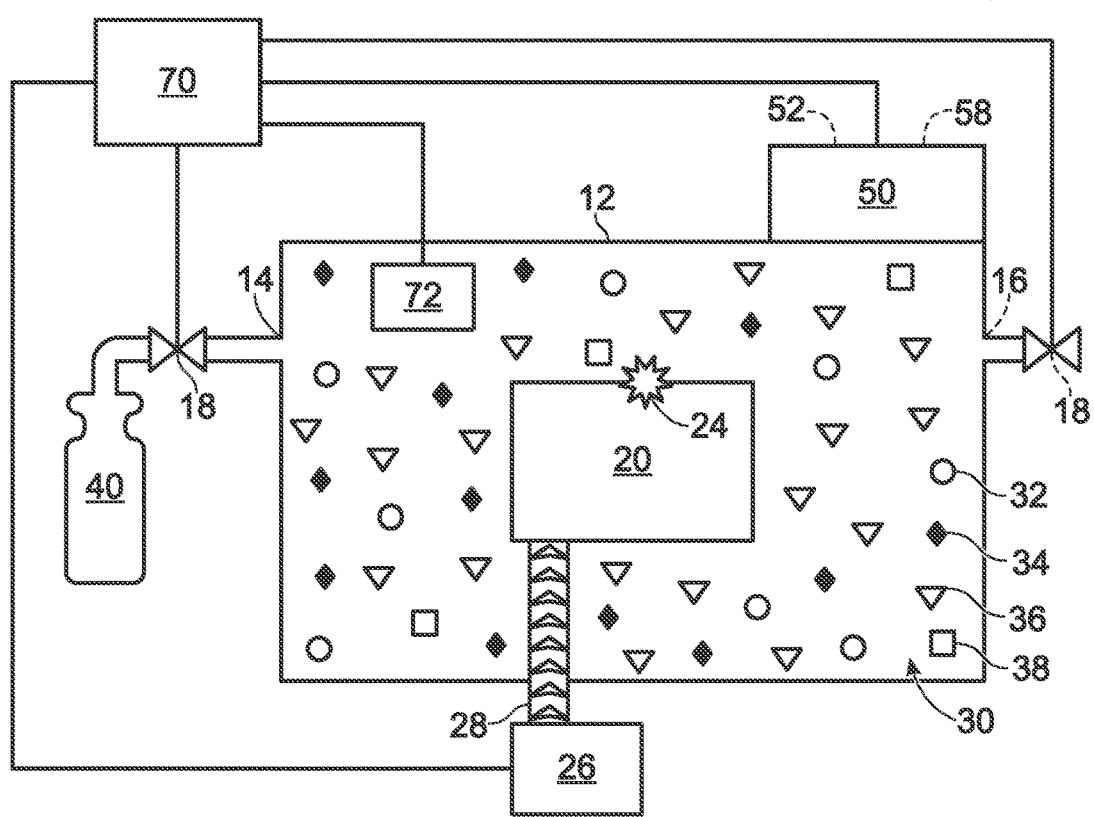
FIG. 1 is a schematic representation of an incendivity test system according to the present disclosure.

The systems and methods described herein can be used to test for ignition hazards without the limitations of the traditional ignition hazard testing techniques. For example, the herein-described systems and methods can be sensitive to various types of ignition hazards without requiring a flammable atmosphere. More specifically, incendivity test systems and methods of the present disclosure are similar to ignitable mixture (flammable gas) test systems and methods, but fundamentally differ by utilizing a non-flammable gas mixture. The ignitable mixture (flammable gas) test systems and methods would not function to produce a result (explosive combustion) without the flammable gas.

With the incendivity test systems and methods of the present disclosure, the test article may be subject to a simulated ignition risk event (e.g., a simulated lightning strike) and if the ignition risk event generates an ignition source at the test article, some of the non-flammable gas mixture will react. The non-flammable gas mixture is selected, configured, and/or formulated such that an ignition source will not generate a self-propagating combustion front (i.e., the gas will not explode due to the ignition source). Only a portion of the non-flammable gas mixture, a portion near the ignition source, will react to the ignition source. The reaction due to the ignition source may be detected by analyzing the gas contents after the ignition risk event. By examining the degree or amount of chemical change to the non-flammable gas mixture, the risk of ignition due to an energy release (the ignition risk event) may be quantified. The risk of ignition may be a binary value (yes/no, pass/fail, etc.) or a value related to the degree or amount of chemical change to the non-flammable gas mixture. Hence, the incendivity test systems and methods of the present disclosure may provide more information about the ignition source (such as the amount of energy released) than traditional ignition hazard testing techniques such as the photographic method or the ignitable mixture (flammable gas) test method.

FIGS. 1-4 illustrate incendivity test systems and methods. In general, in the drawings, elements that are likely to be included in a given embodiment are illustrated in solid lines, while elements that are optional or alternatives are illustrated in dashed lines. However, elements that are illustrated in solid lines are not essential to all embodiments of the present disclosure, and an element shown in solid lines may be omitted from a particular embodiment without departing from the scope of the present disclosure. Elements that serve a similar, or at least substantially similar, purpose are labelled with numbers consistent among the figures. Like numbers in each of the figures, and the corresponding elements, may not be discussed in detail herein with reference to each of the figures. Similarly, all elements may not be labelled or shown in each of the figures, but reference numerals associated therewith may be used for consistency. Elements, components, and/or features that are discussed with reference to one or more of the figures may be included in and/or used with any of the figures without departing from the scope of the present disclosure.

FIG. 1 illustrates an incendivity test system 10 that may be utilized to test the incendivity of a test article 20 that is subject to an ignition risk event (an energy discharge). The test system 10 includes a non-flammable gas mixture 30 to sense an ignition source 24 generated at the test article 20, an energy source 26 configured to apply the energy discharge to the test article 20 to potentially generate the ignition source 24, and a detection device 50 configured to measure an amount of one or more indicator species in the non-flammable gas mixture after the energy discharge. Incendivity is the ability to cause ignition of a flammable substance such as a flammable environment. Hence, the incendivity test system 10 may be referred to as a flammability test system, an ignition risk test system, and/or an ignition hazard test system.

Generally, the test system 10 is configured to identify the presence of, and/or verify the absence of, ignition sources 24 associated with equipment, devices, and/or apparatuses operated in a combustible environment and/or near combustible materials. More specifically, the test system 10 may be configured to detect ignition sources 24 generated on the test article 20 by the ignition risk event (the energy discharge generated by the energy source 26) that simulates actual and/or potential operating conditions and/or uncontrolled events. For example, the energy discharge may be a simulated lightning strike, heat, an electrical discharge, an electrical voltage, an electrical current, an electrical arc, and/or a combustion event (e.g., heat, flame, fire). Examples of ignition sources 24 that may be generated include an electrical arc, a spark, a hot surface, a hot particle ejection, an electrostatic discharge, and a flame.

The test article 20 may be equipment, a device, and/or an apparatus that may operate near combustible materials and/or in combustible environments where uncontrolled ignition sources could be hazardous. The test article 20 also may be a portion, a component, and/or a model of such equipment, device, and/or apparatus. The equipment, device, and/or apparatus may be associated with one or many industries such as transportation, aerospace, chemical processing, petroleum production, mining, power production, forestry, and/or agriculture. For example, the test article 20 may be, may represent, and/or may be a component of a transport vehicle (e.g., a truck, an aircraft, a rocket), an aerospace component, an aircraft skin, an aircraft frame, a wing, a fuel handling component, a fuel system, a fuel tank, a fuel pump, a ventilator component, a ventilation system, mining equipment, dust handling equipment, and/or an electrical enclosure. Generally, the test article 20 has a solid form, though the test article 20 may include liquid and/or gaseous elements. The test article 20 may include one or more of metal, aluminum, plastic, and fiber-reinforced composite material.

The energy source 26 is configured to discharge energy into, at, and/or to the test article 20 to test whether the discharged energy generates the ignition source 24 at the test article 20. The energy source 26 may be a simulated or actual operating condition such as a lightning strike, an electrical charge simulating static charge build-up, heat simulating environmental conditions (e.g., ambient operating conditions, proximate decomposition and/or combustion, and/or operation of a neighboring engine), and/or electromagnetic radiation simulating an operating environment. The energy source 26 may include, and/or may be, a lightning simulator, a heater, a heat source, a flame, an electrical power source, an electrical voltage source, an electrical current source, and/or an electrical arc generator. In FIG. 1, the discharged energy is indicated by energy transmission 28. Energy transmission 28 may be via a conduit, a cable, and/or a conductor, and may span a gap between the energy source 26 and the test article 20. The energy source 26 may be separated and/or external from the test article 20 (as illustrated in the example of FIG. 1). In some embodiments, the test article 20 may include the energy source 26 and/or the test article 20 may be the energy source 26 (for example, a test article 20 may be a battery and the test system 10 may be configured to test the battery under normal operating conditions).

The test system 10 and/or the energy source 26 are configured to avoid directly reacting the non-flammable gas mixture 30 with the energy discharge. In one arrangement, the test system 10 and/or the energy source 26 may be configured to apply the energy discharge to the test article 20 at an application site isolated from the non-flammable gas mixture 30. For example, the energy transmission 28 may include electrical cables which convey a voltage and/or carry a current, and that are electrically insulated from the non-flammable gas mixture 30. As another example, the test article 20 may include an exterior and/or an interior (which may be fluidically isolated from one another). The non-flammable gas mixture 30 may contact one of the exterior and interior and the application site of the discharged energy may be on the other side (exterior or interior). More specifically, the test article 20 may have an interior fluidically isolated from the exterior (e.g., a tank, a chamber, a canister, a vessel) with non-flammable gas mixture 30 contacting the exterior (or a portion thereof) and a flammable material within the interior (for example, a flammable gas or aerosol filling the interior, or a volatile, flammable liquid partially filling the interior). Igniting the flammable material discharges energy as the material combusts. This energy may be discharged to the interior of the test article 20 while the non-flammable gas mixture 30 is at the exterior of the test article 20 to indicate whether the energy discharge creates any ignition sources 24 at the exterior of the test article 20.

The test system 10 may include a test chamber 12 that is configured to at least partially enclose the test article 20. The test chamber 12 may be configured to hold the non-flammable gas mixture 30 and/or fluidically isolate the test article 20 and/or the non-flammable gas mixture 30 from an ambient environment (e.g., air). The test chamber 12 may be a sealed chamber, an enclosed space, and/or a partitioned space.

In FIG. 1, the test article 20 is enclosed in the test chamber 12 with the non-flammable gas mixture 30. The test chamber 12 may enclose the entirety or a portion of the test article 20. The non-flammable gas mixture 30 may contact the entirety or a portion of the test article 20. The test article 20 may be inserted into the test chamber 12 and/or the test chamber 12 may be assembled around the test article 20. The test chamber 12 may partially or completely enclose one or more other components of the test system 10. For example, the energy source 26, the detection device 50, and/or a controller 70 (described further herein) may be within the test chamber 12.

The test chamber 12 may include a gas inlet port 14 and/or a gas outlet port 16 configured to permit gas to enter and/or exit the test chamber 12. In some embodiments, the test chamber 12 may include a single port that serves as both a gas inlet port 14 and a gas outlet port 16. The gas inlet port 14 and/or the gas outlet port 16 may be associated with one or more valves 18 that are configured to open and/or close the gas inlet port 14 and/or the gas outlet port 16.

The test chamber 12 may be gas tight in some configurations (e.g., when the gas inlet port(s) 14, the gas outlet port(s) 16, and any doors, windows, covers, etc. are closed and/or sealed). The test chamber 12 may be configured to isolate the test article 20, the non-flammable gas mixture 30, and/or other components within the test chamber 12 from outside influences and vice versa. For example, the test chamber 12 may be a gas-tight chamber, an electromagnetic shield, and/or a safety shield. As another example, the test chamber 12 may be configured to avoid mixing of the non-flammable gas mixture 30 with the ambient environment.

The test system 10 may include a gas source 40 configured to supply the non-flammable gas mixture 30 to the test article 20 and/or the test chamber 12. The gas source 40 may be fluidically connected to the test chamber 12 via the gas inlet port 14. The flow path from the gas source 40 to the test article 20 and/or the test chamber 12 may include a valve 18 that is configured to control the flow of the non-flammable gas mixture 30.

The test chamber 12 may be filled by flushing the test chamber 12 with the non-flammable gas mixture 30 (e.g., by flowing several volumes of the test chamber 12 through the test chamber 12 in a manner to flush out the air or other gas initially filling the test chamber 12). Additionally, or alternatively, the test chamber 12 may be filled by evacuating the air or other gas that initially fills the test chamber 12 and by flowing the non-flammable gas mixture 30 into the test chamber 12.

In some embodiments, the test system 10 may be configured to place the test article 20 in contact with a flowing stream of the non-flammable gas mixture 30. Such embodiments may include the test chamber 12 to direct the stream to and/or around the test article 20 or may not include the test chamber 12. The stream of the non-flammable gas mixture 30 may contact a portion or the entirety of the test article 20. The stream of the non-flammable gas mixture 30 may be a recirculating or non-recirculating stream.

The non-flammable gas mixture 30 includes a thermally reactive reagent 32. The thermally reactive reagent 32 is thermally reactive, i.e., the thermally reactive reagent 32 undergoes reaction, e.g., a combustion reaction (i.e., a fuel-oxidant reaction with an oxidant 34) and/or a thermal decomposition, in response to sufficient heat to produce one or more species of reaction products 38.

Due to the presence of the thermally reactive reagent 32, the non-flammable gas mixture 30 is thermally reactive and sensitive to the ignition source 24 that may be created by the ignition risk event (the energy discharge of the energy source 26). However, the non-flammable gas mixture 30 is selected, configured, and/or formulated to not be flammable or explosive. The non-flammable gas mixture 30 is reactive enough to produce a measurable change in gas contents in the presence of the ignition source 24 without being so reactive as to produce a sustained flame, self-propagating combustion, or explosion. For example, the non-flammable gas mixture 30 may be a fuel-air mixture that is too lean to support continued combustion (i.e., below the lower flammability limit). Because the non-flammable gas mixture 30 does not explode, produce a sustained flame, or yield self-propagating combustion, the non-flammable gas mixture 30 does not present a significant explosion risk or an explosion risk that is as significant as traditional flammable gas mixtures utilized for ignitable mixture (flammable gas) test systems.

With the non-flammable gas mixture 30 in contact with the test article 20, the test article 20 may be tested for the ability to produce the ignition source 24 in response to the ignition risk event (i.e., tested for the incendivity of the test article 20) by measuring the change in gas contents of the non-flammable gas mixture 30 after the ignition risk event. The thermal reaction of the thermally reactive reagent 32 due to the ignition source 24 occurs through the same physical mechanism (heat-induced chemical reaction) as does a fuel vapor or other combustible environment that may be present at the test article 20 in use. Hence, if the thermally reactive reagent 32 sufficiently reacts in response to the ignition source 24, an actual combustible environment would be expected to react as well.

The thermally reactive reagent 32 may be a combustion fuel, i.e., a reagent that combusts in the presence of the oxidant 34. The thermally reactive reagent 32 may be a compound that thermally decomposes in the presence of the ignition source 24. In such reaction systems, an oxidant 34 may not be needed. Examples of combustion fuels include a hydrocarbon fuel, a flammable gas, molecular hydrogen, methane, propane, gasoline, kerosene, and ethylene. Other examples of the thermally reactive reagent 32 include a halocarbon (a compound with a halogen-carbon bond) such as an alkyl halide, a chlorocarbon, a fluorocarbon, a bromocarbon, a chlorofluorocarbon, chloroethane, and methyl bromide.

The non-flammable gas mixture 30 is generally gaseous and may include gas and/or an aerosol of liquids and/or solids (e.g., the non-flammable gas mixture 30 may include an aerosol of the thermally reactive reagent 32). The thermally reactive reagent 32 may be in the form of a gas, a vapor, and/or an aerosol.

The non-flammable gas mixture 30 may include the oxidant 34, in particular if the thermally reactive reagent 32 is a combustion fuel or is otherwise selected, configured, and/or formulated to react with the oxidant 34. Together, the thermally reactive reagent 32 and the oxidant 34 may be referred to as a reactive system. The oxidant 34 may be in the form of a gas, a vapor, and/or an aerosol. For example, the non-flammable gas mixture 30 may include an aerosol of the oxidant 34. Examples of the oxidant 34 include molecular oxygen, nitrous oxide, and hydrogen peroxide. Examples of reactive systems include combustion fuels and molecular oxygen, and halocarbons and molecular oxygen.

The non-flammable gas mixture 30 may include a diluent 36. The diluent 36 is generally a gas and does not significantly participate in the reaction with the thermally reactive reagent 32 to produce the reaction product 38. Generally, the diluent 36 is inert and/or non-reactive. The diluent 36 may be selected, configured, and/or formulated for lack of reactivity with other components of the non-flammable gas mixture 30 and/or for lack of interference with the reaction to produce the reaction product 38. The diluent 36 may be selected, configured, and/or formulated to quench combustion and/or a flame front in the non-flammable gas mixture 30. For example, the diluent 36 may have a high heat capacity and/or a low thermal conductivity which may limit the flammability of the non-flammable gas mixture 30. Examples of the diluent 36 include an inert gas, nitrogen, argon, and helium.

Mixtures of combustion fuels and oxidants 34 have a flammability range in which the mixture may be ignited (at a given pressure and temperature). Outside of the flammability range, the mixture cannot be ignited, without changing the conditions such as increasing the temperature and/or the pressure. The flammability range may be expressed as a ratio of the combustion fuel to oxidant concentrations, and/or a concentration range of the combustion fuel in an oxidant-fuel mixture. An oxidant-fuel mixture has a stoichiometric ratio for complete burning of the oxidant and the combustion fuel. If the amount of combustion fuel is below the stoichiometric amount, the mixture is called lean. If the amount of combustion fuel is above the stoichiometric amount, the mixture is called rich. Unless otherwise stated, the flammability range as used herein is expressed as a mass concentration ratio of combustion fuel to oxidant.

The flammability range is delineated by a lower flammability limit (also called a lean ignition limit) and an upper flammability limit (also called a rich ignition limit). Below the lower flammability limit, the oxidant-fuel mixture does not contain enough combustion fuel to support a self-propagating combustion wave. Above the upper flammability limit, the oxidant-fuel mixture does not contain enough oxidant to support a self-propagating combustion wave.

Examples of non-flammable gas mixtures 30 include mixtures below the lower flammability limit and mixtures above the upper flammability limit. Mixtures above the upper flammability limit may be diluted by contaminant gas (such as air) to form a flammable gas mixture (i.e., with a lower concentration of combustion fuel that is within the flammability limits). Mixtures below the lower flammability limit may not be transformed by common contaminant gases to form a flammable gas mixture. One example of a non-flammable gas mixture 30 that is below the lower flammability limit is a non-flammable gas mixture 30 that includes a volume fraction of ethylene of less the 2.7% (the lower flammability limit at room temperature and pressure), less than 2.5%, about 2%, and/or greater than 0.1% in air. As another example, the non-flammable gas mixture 30 may include a volume fraction of chloroethane of less than 3.8% (the lower flammability limit at room temperature and pressure), about 1%, and/or greater than 0.1% in air. As yet another example of a non-flammable gas mixture 30, methyl bromide is not generally flammable except in the presence of strong oxidizers or strong ignition sources. The non-flammable gas mixture 30 may include a small amount of methyl bromide, e.g., a volume fraction of 0.01%, in air.

Reaction products 38 may be the result of complete combustion of the thermally reactive reagent 32, the result of partial combustion of the thermally reactive reagent 32, the result of thermal decomposition of the thermally reactive reagent 32, and/or chemical species that are derived from the complete or partial combustion products and/or the thermal decomposition products. Examples of complete combustion products include water and carbon dioxide (e.g., for combustion of a hydrocarbon). Examples of partial combustion products include formaldehyde and carbon monoxide (e.g., for combustion of a hydrocarbon). Other examples of reaction products 38 (e.g., for halocarbons) include hydrochloric acid, hydrofluoric acid, hydrobromic acid, carbonyl difluoride, carbonyl dichloride (also called phosgene and carbon oxychloride), carbonyl dibromide (also called carbon oxybromide), molecular fluorine, molecular chlorine, and molecular bromine. The non-flammable gas mixture 30 may include relatively little reaction product 38 and/or may be essentially free of reaction product 38 prior to exposure of the non-flammable gas mixture 30 to the ignition source 24.

In some embodiments, the non-flammable gas mixture 30 includes an indicator species (e.g., thermally reactive reagents 32 and/or reaction products 38) that is easy to identify and/or distinct from background and/or contamination sources. For example, the thermally reactive reagent 32 may be a halocarbon. Halocarbons may be unique or rare in a typical environment such that the presence of the compound indicates the presence of the non-flammable gas mixture 30. Similarly, the reaction products of halocarbons may be unique or rare in a typical environment. When a molecule of interest is uncommon in the background environment, the analysis of the gas components may be more sensitive to that component because of the lack of background signal and/or the lack of background noise.

Non-flammable gas mixtures 30 may be selected, configured, and/or formulated such that the reaction to produce the reaction product 38 occurs at or above a threshold reaction energy at suitable conditions. The threshold energy may be less than 1,000 µJ (microjoules), less than 500 µJ, less than 200 µJ, less than 100 µJ, greater than 10 µJ, greater than 50 µJ, greater than 100 µJ, greater than 200 µJ, and/or about 200 µJ. Suitable conditions may include standard pressure and temperature, reduced pressure and/or temperature as compared to standard pressure and temperature, and/or elevated pressure and/or temperature as compared to standard pressure and temperature corresponding to operating and/or storage conditions of the test article 20 (or equipment, devices, and/or apparatuses represented by the test article 20). Suitable conditions may simulate environments such as operating and/or storage conditions on the surface of the Earth (e.g., hot conditions in hot climates, cold conditions in cold climates), in the sky (e.g., cold and low pressure conditions at altitude), and/or below ground (e.g., hot conditions in tunnels). For example, suitable conditions may include a temperature of less than 200° C., less than 150° C., less than 100° C., less than 80° C., less than 50° C., less than 30° C., greater than −40° C., greater than −20° C., greater than 0° C., greater than 10° C., about 20° C., and/or about 40° C. Suitable conditions may include a pressure of greater than 50 kPa (kilopascals), greater than 70 kPa, greater than 90 kPa, greater than 100 kPa, less than 200 kPa, less than 150 kPa, less than 120 kPa, less than 100 kPa, about 70 kPa, and/or about 100 kPa. The selection, formulation, and/or composition of the non-flammable gas mixture 30 and its components may affect the threshold reaction energy. The minimum reaction energy of the non-flammable gas mixture 30 may be calibrated and/or verified by subjecting the non-flammable gas mixture 30 to a controlled-energy ignition source such as a controlled electrical arc of a known ignition energy.

The non-flammable gas mixture 30 may include one or more species of thermally reactive reagents 32, oxidants 34, and/or diluents 36. Multiple species and/or multiple reactive systems may be advantageous to be sensitive to ignition sources of different types and/or different energies. For example, one reactive system (a species of thermally reactive reagent 32 and an optional species of oxidant 34) may be most sensitive to hot particle emissions while another reactive system may be most sensitive to an electrical arc. In embodiments with multiple thermally reactive reagents 32, each thermally reactive reagent 32 may be selected, configured, and/or formulated to react with at least one of the oxidants 34 and/or the same oxidant 34 to produce a corresponding reaction product 38.

The test system 10 includes the detection device 50 that is configured to detect one or more indicator species of the non-flammable gas mixture 30 after the ignition risk event is applied to the test article 20 in contact with the non-flammable gas mixture 30. The detection device 50 is configured to detect the reaction (if any) and/or the extent of the reaction due to the ignition source 24 by detecting the indicator species. The indicator species detected may be the thermally reactive reagent 32, the oxidant 34, and/or the reaction product 38. The presence and/or an increase of reaction products 38, and/or the decrease of reactants (e.g., the thermally reactive reagent 32 and/or the oxidant 34) indicate the reaction and/or the extent of reaction of the thermally reactive reagent 32 due to the presence of the ignition source 24.

The detection device 50 may measure an amount of one or more indicator species and/or a ratio of indicator species. As used herein, the detection, measurement and/or determination of an amount of a chemical species may include detection, measurement and/or determination of the presence, the presence above a threshold level, the quantity relative to a control component, and/or the absolute quantity. Control components may be another indicator species, the thermally reactive reagent 32, the oxidant 34, the diluent 36, the reaction product(s) 38, and/or another chemical species in the non-flammable gas mixture 30 (before or after reaction). For example, the detection device 50 may measure a ratio of the reaction product 38 to the thermally reactive reagent 32 and/or may measure a ratio of two reaction products 38. A ratio of the indicator species to another gas component (e.g., a product to reactant ratio or a product to product ratio) may be more robust than detecting the indicator species alone (e.g., a ratio may be resilient to gas leaks in the test chamber 12). Amounts and/or quantities of chemical species may be measured and/or determined relative to mass, volume, pressure, and/or moles (number of molecules or atoms). Unless otherwise specified, amounts and quantities are expressed in mass units (e.g., mass, mass concentration, mass ratio, etc.). Control components may be another indicator species Because the non-flammable gas mixture 30 is non-flammable, only a portion of the non-flammable gas mixture 30 will react in response to the ignition source 24. The portion is related to the physical size of the ignition source, the duration of the ignition source, and the energy content of the ignition source. The thermally reactive reagent 32 in the non-flammable gas mixture 30 will react in a localized, relatively small volume that is related to the size and energy content of the ignition source and the nature of the reaction (e.g., combustion and/or thermal decomposition) of the thermally reactive reagent 32. The reaction volume may be referred to as a reaction kernel and/or a combustion kernel. The reaction volume may be less than 10 mL (milliliter), less than 1 mL, or less than 0.1 mL, and typically is greater than 0.000001 mL (1 nanoliter). The total volume of the non-flammable gas mixture 30 in contact with the test article 20 is related to the size of the test article 20 (at least the size of the portion in contact with the non-flammable gas mixture 30). Some test articles may be very large (e.g., an aircraft wing). Typical volumes of the non-flammable gas mixture 30 include greater than 1 L (liter), greater than 10 L, greater than 100 L, or greater than 1,000 L, and typically is less than 100,000 L (100 cubic meters). Thus, the reaction volume of the non-flammable gas mixture 30 may be less than one thousandth or less than one millionth of the total volume of the non-flammable gas mixture 30.

Because of the small reaction volume of the non-flammable gas mixture 30 and because the thermally reactive reagent 32 may be included in the non-flammable gas mixture 30 at a volume concentration of less than 10% (or less than 1%), the indicator species (e.g., the thermally reactive reagent 32 and/or the reaction product 38) may have a change in concentration, relative to the non-flammable gas mixture 30 before the ignition risk event, that may be in the range of parts per million or parts per billion. Hence, the detection device 50 may be configured to measure concentrations and/or absolute changes in concentrations at the level of parts per million or parts per billion.

Detection devices 50 may be high sensitivity gas analysis devices adapted to measure the (potentially reacted) non-flammable gas mixture 30. For example, illustrated in more detail in FIG. 2, the detection device 50 may be a gas sampling detection device 52 such as a mass spectrometer, a gas chromatograph, or a gas chromatography mass spectrometer. As another example, illustrated in more detail in FIG. 3, the detection device 50 may be an optical detection device 58 such as an optical spectrometer (that may measure absorbance, transmittance, reflectance, scattering, spectrum, luminescence, fluorescence, and/or phosphorescence), a laser-induced fluorescence (LIF) apparatus, a planar laser-induced fluorescence (PLIF) apparatus, a laser-excited atomic fluorescence (LEAF) apparatus, and a Fourier transform infrared (FTIR) spectrometer.

Figure 2:
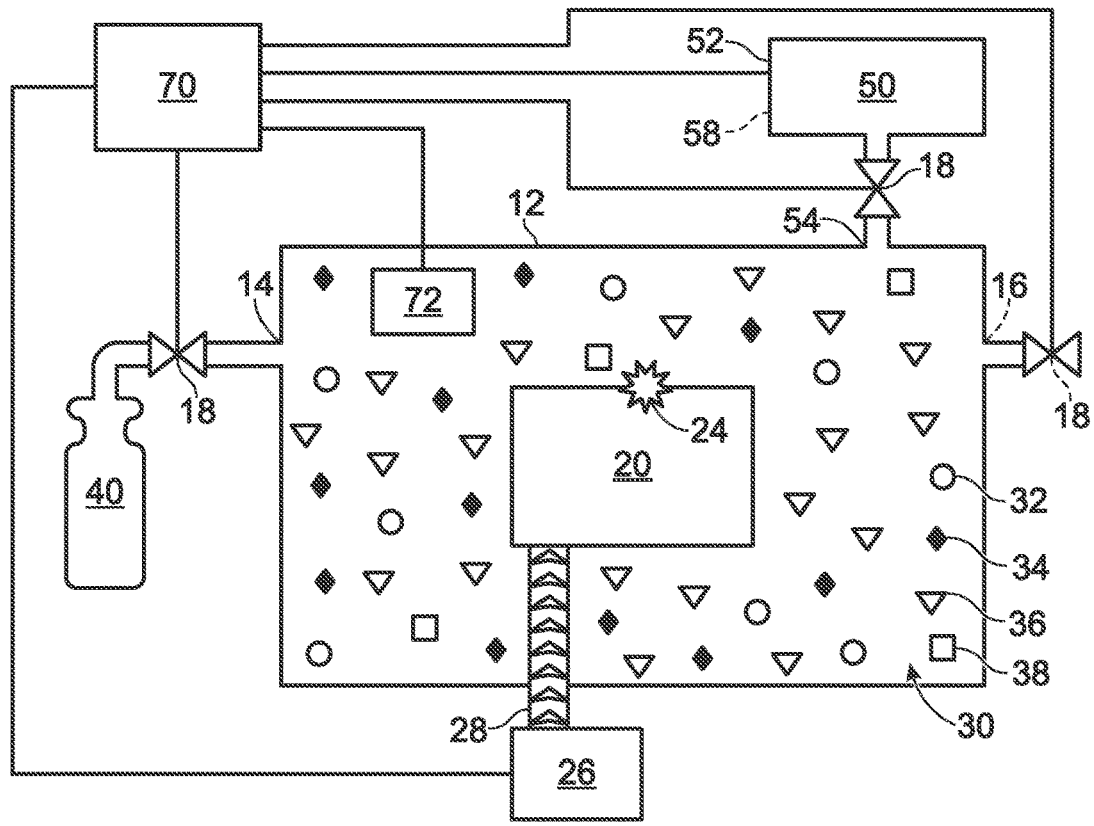
FIG. 2 is a schematic representation of an example of an incendivity test system according to the present disclosure.

As shown in FIG. 2, the gas sampling detection device 52 (e.g., the mass spectrometer, the gas chromatograph, or the gas chromatography mass spectrometer) may be configured to sample a portion (or the entirety) of the non-flammable gas mixture 30 after the ignition risk event may cause the ignition source 24 at the test article 20 and the consequent reaction of the reaction volume of the non-flammable gas mixture 30. The gas sampling detection device 52 may be configured to sample unreacted non-flammable gas mixture 30 and/or the non-flammable gas mixture 30 before the ignition risk event. The gas sampling detection device 52 may be fluidically connected to the test chamber 12 via a gas sample port 54 of the test chamber 12. The flow path from the test chamber 12 to the gas sampling detection device 52 may include a valve 18 that is configured to control the flow of the non-flammable gas mixture 30.

A mass spectrometer is an analytical instrument that analyzes a sample by ionizing chemical species in the sample and subjecting the ionized species to electric and magnetic fields to identify mass to charge ratios of the ionized species. The ionized species typically are fragments of the molecular species of the sample. The chemical species may be identified by the mass to charge ratios and/or the pattern of ionized fragments.

A gas chromatograph is an analytical instrument that separates and/or analyzes gaseous and/or vaporous chemical species in a sample (and/or derived from a sample). Gas chromatographs typically detect the retention time of the chemical species travelling through a column.

A gas chromatography mass spectrometer includes a gas chromatograph column input stage and a mass spectrometer detection stage. The gas chromatograph input provides separation of components of the sample prior to mass spectrometry such that gas components may be more specifically determined (e.g., by retention time and mass to charge ratio) than with an ordinary gas chromatograph (e.g., by retention time) or an ordinary mass spectrometer (e.g., by mass to charge ratio).

Figure 3:
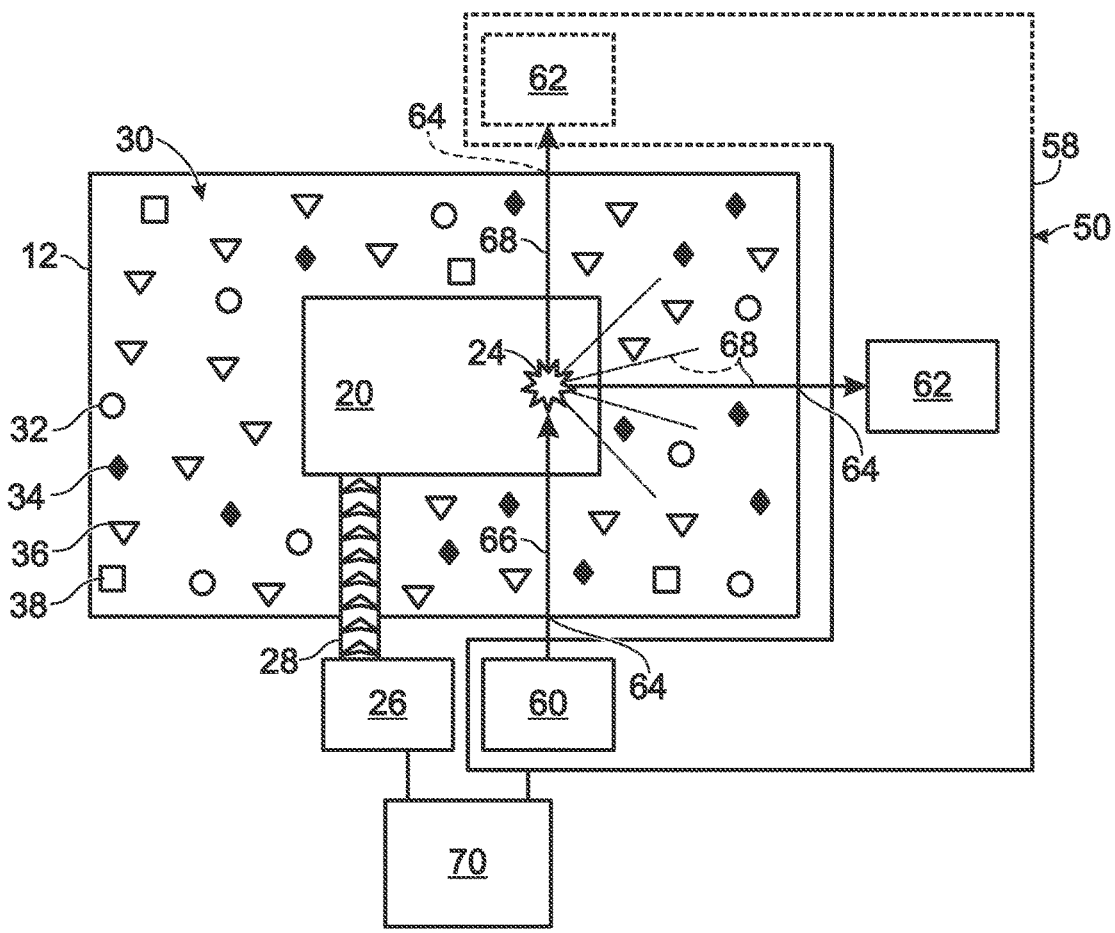
FIG. 3 is a schematic representation of another example of an incendivity test system according to the present disclosure.

As also shown in FIG. 2, the optical detection device 58 (e.g., the optical spectrometer, the LIF apparatus, the PLIF apparatus, the LEAF apparatus, or the FTIR spectrometer) may be configured to sample and measure a portion (or the entirety) of the non-flammable gas mixture 30 in a configuration similar to the gas sampling detection device 52. Additionally or alternatively, and as shown in FIG. 3, the optical detection device 58 may be configured to measure the non-flammable gas mixture 30 in situ, proximate to the test article 20.

The optical detection device 58 may include one or more components within the optional test chamber 12 and may include one or more components outside of the test chamber 12. For components located outside of the test chamber 12, those components may be in optical communication with the non-flammable gas mixture 30 in the test chamber 12 via a window 64 in the test chamber 12 (e.g., a transparent wall).

The optical detection device 58 generally includes a light source 60 and an optical detector 62. The light source 60 is configured to interrogate the non-flammable gas mixture 30 in the test chamber 12 and/or proximate to the test article 20 with an input light beam 66. The light source 60 may include, and/or may be, a laser, a lamp, or an LED (light emitting diode). The light source 60 may generate and/or the input light beam 66 may include light with a wavelength in the ultraviolet (UV), visible, infrared (IR), and/or far infrared (FIR). For example, the light may have a wavelength greater than 100 nm (nanometers), 200 nm, greater than 400 nm, greater than 600 nm, greater than 800 nm, greater than 2,000 nm, greater than 10,000 nm, less than 20,000 nm, less than 4,000 nm, less than 1,000 nm, less than 800 nm, less than 400 nm, and/or less than 300 nm.

The optical detector 62 is configured to detect output light 68 from the (potentially reacted) non-flammable gas mixture 30 due to interaction with the input light beam 66. The optical detector 62 may be sensitive to light, and the output light 68 may have a wavelength in the ultraviolet (UV), visible, infrared (IR), and/or far infrared (FIR). For example, the light may have a wavelength greater than 100 nm (nanometers), 200 nm, greater than 400 nm, greater than 600 nm, greater than 800 nm, greater than 2,000 nm, greater than 10,000 nm, less than 20,000 nm, less than 4,000 nm, less than 1,000 nm, less than 800 nm, less than 400 nm, and/or less than 300 nm. The optical detector 62 may be configured to detect the light of the input light beam 66 (e.g., for transmission, absorbance, reflection, and scattering (nephelometry) measurements) and/or to reject the light of the input light beam 66 (e.g., for luminescence, fluorescence, phosphorescence, and Raman scattering measurements).

The optical detection device 58 may be configured to determine transmission, reflection, absorption, scattering, luminescence, fluorescence, and/or phosphorescence of the non-flammable gas mixture 30. In scattering, fluorescence, or phosphorescence mode, the optical detection device 58 has the light source 60 and the optical detector 62 arranged non-collinearly, for example facing orthogonal light paths as shown in the example of FIG. 3 (with the optical detector 62 in solid lines). The optical detector 62 is configured to detect the output light 68 that emerges from a sample of the non-flammable gas mixture 30 due to interaction with the input light beam 66. For example, the output light 68 may be due to scattering (e.g., Rayleigh or Raman scattering) and/or optical emission (e.g., luminescence, fluorescence, and/or phosphorescence emission).

In transmission mode (e.g., for transmission or absorbance measurements), the optical detection device 58 is arranged such that the non-flammable gas mixture 30 (or a sample of the non-flammable gas mixture 30) is optically between the light source 60 and the optical detector 62. For example, the light source 60 and the optical detector 62 may be on opposite sides of the test chamber 12 as shown in FIG. 3 (with the optical detector 62 in dotted lines). The optical detector 62 is configured to detect the input light beam 66 that is transmitted through the sample of the non-flammable gas mixture 30. The input light beam 66 is transformed by interaction with the sample into the output light 68 in the form of a transmitted beam and/or an attenuated beam.

A LIF apparatus, a PLIF apparatus, and a LEAF apparatus are analytical apparatuses configured to illuminate a sample containing an indicator species (a molecule or atom) with laser light (the input light beam 66) tuned to excite fluorescence in the indicator species. The fluorescence emission (the output light 68) is detected by the optical detector 62 that is configured to detect light of the fluorescence emission and reject light of the input light beam 66. The spectra, intensity, and lifetime of the fluorescence emission may provide sensitive discrimination of the indicator species over other background species and/or may provide information about the state of the indicator species and/or the local environment near the indicator species. In a PLIF apparatus, the laser light is scanned and/or spread into a light sheet and the fluorescence emission may be detected by an imaging detector.

A FTIR spectrometer is an analytical instrument that measures the infrared absorption or emission spectrum of a sample. The FTIR spectrometer simultaneously collects high spectral resolution data over a wide spectral range. The high spectral resolution and wide spectral range may provide sensitive discrimination of different indicator species in the sample.

Returning generally to FIG. 1, the test system 10 may include a controller 70 configured and/or programmed to control the operation of the test system 10 as a whole and/or individual components of the test system 10. The controller 70 may be configured and/or programmed (a) to discharge the energy source 26 to apply the energy discharge to the test article 20, (b) to measure the presence and/or amount of the indicator species in the non-flammable gas mixture 30 with the detection device 50, and/or (c) to determine an incendivity of the test article 20 in response to the energy discharge based upon the presence and/or amount of the indicator species. The controller 70 may be configured and/or programmed to operate valves 18 at the gas inlet port 14, the gas outlet port 16, and/or at the gas sample port 54 to respectively control gas entering the test chamber 12, gas exiting the test chamber 12, and/or gas sampled by the detection device 50. The controller 70 may be configured and/or programmed to perform any of the methods described herein. The controller 70 may include a computer, an embedded controller, a programmable logic device, and/or a field-programmable gate array.

The test system 10 may include a controlled ignition source 72 that is configured to discharge energy (e.g., create an ignition source such as an arc) in the non-flammable gas mixture 30 sufficient to react the thermally reactive reagent 32 in the non-flammable gas mixture 30. The controlled ignition source 72 may be configured to discharge energy into the non-flammable gas mixture 30 in the optional test chamber 12 and/or at a position configured to be detected by the detection device 50 (e.g., upstream in a flowing stream of the non-flammable gas mixture 30).

The controlled ignition source 72 may be controlled by the controller 70. For example, the controller may be configured and/or programmed to initiate the energy discharge of the controlled ignition source 72 and/or to terminate the energy discharge of the controlled ignition source 72.

The controlled ignition source 72 may be configured to discharge a predetermined amount of energy into the non-flammable gas mixture 30 and/or an amount of energy configured to cause the thermally reactive reagent 32 to react. A controlled ignition source 72 that provides a predetermined and/or controllable amount of energy into the non-flammable gas mixture 30 may be referred to as a controlled-energy ignition source. The controlled ignition source 72 may discharge an energy of less than 1,000 μJ, less than 500 μJ, less than 200 μJ, less than 100 μJ, greater than 10 μJ, greater than 50 μJ, greater than 100 μJ, greater than 200 μJ, and/or about 200 μJ. The controlled ignition source 72 may produce an electrical arc, a spark, a hot surface, a hot particle ejection, an electrostatic discharge, and/or a flame.

Figure 4:
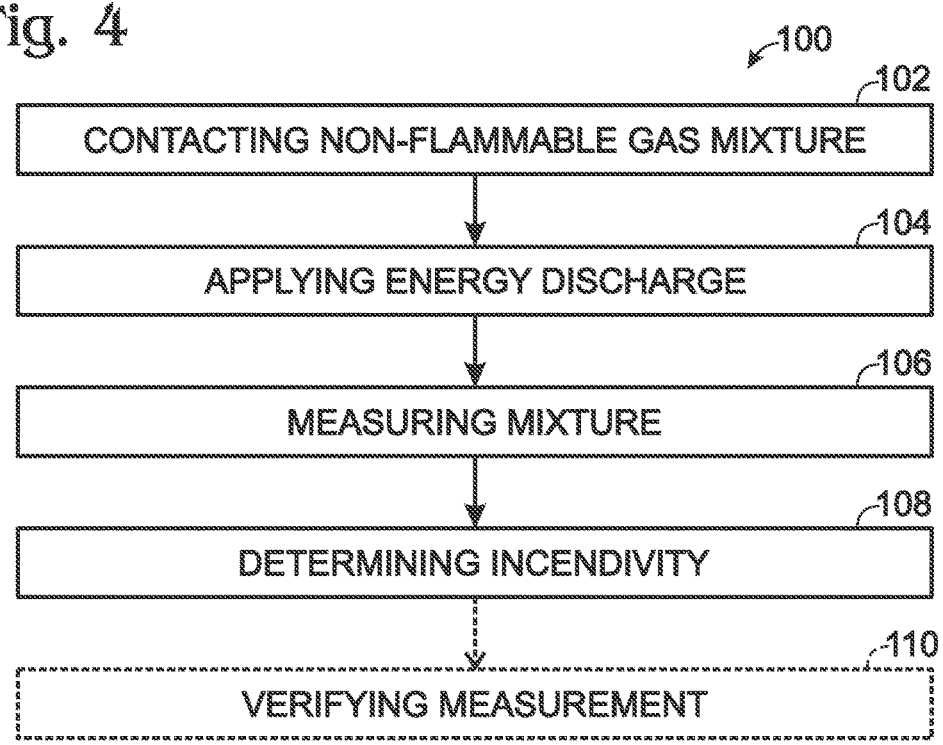
FIG. 4 is a schematic representation of incendivity test methods according to the present disclosure.

FIG. 4 illustrates incendivity test methods 100. Methods 100 may be referred to as flammability test methods, ignition risk test methods, and/or ignition hazard test methods. Methods 100 include contacting 102 a test article (such as test article 20) with a non-flammable gas mixture (such as non-flammable gas mixture 30), applying 104 an energy discharge to the test article while the test article is in contact with the non-flammable gas mixture, then measuring 106 an amount of one or more components (e.g., indicator species as described herein) of the non-flammable gas mixture to determine the response of the non-flammable gas mixture to the energy discharge, and determining 108 an incendivity of the test article in response to the energy discharge based upon the amount of the one or more components measured. Methods 100 may include using the non-flammable gas mixture to test the incendivity to the test article and/or using the test system 10 to test the incendivity of the test article.

Contacting 102 may include contacting the test article with the non-flammable gas mixture in a test chamber (such as test chamber 12). Contacting 102 may include filling the test chamber with the non-flammable gas mixture and/or creating suitable conditions for the non-flammable gas mixture in the test chamber. Suitable conditions such as pressure, temperature, and simulated operating environments are discussed further herein with respect to the non-flammable gas mixture 30.

Contacting 102 may include flowing a stream of the non-flammable gas mixture over the test article such that the non-flammable gas mixture substantially or completely displaces other gases from contact with the test article (at least at a portion of the test article). The stream of the non-flammable gas mixture may contact a portion or essentially the entirety of the test article. The stream of the non-flammable gas mixture may be a recirculating or non-recirculating stream. In embodiments where the test article is contacted by a stream of the non-flammable gas mixture, the gas analysis (e.g., measuring 106) is generally performed at the point of an ignition source (e.g., the ignition source 24) generated by the applying 104 the energy discharge or downstream from the ignition source. For example, gas analysis may be performed downstream from the test article. If the stream of the non-flammable gas mixture does not recirculate, the gas analysis is downstream from the ignition source and/or the test article.

The non-flammable gas mixture includes a thermally reactive reagent, such as the thermally reactive reagent 32, that reacts to an ignition source (such as ignition source 24) generated by the applying 104 the energy discharge. The thermally reactive reagent reacts to produce one or more reaction products such as reaction products 38. The non-flammable gas mixture may include an oxidant (such as oxidant 34) that reacts with the thermally reactive reagent, and/or may include a diluent such as diluent 36.

Methods 100 may include preparing the non-flammable gas mixture by mixing the thermally reactive reagent with one or more oxidants and one or more diluents. Methods 100 may include preparing the non-flammable gas mixture by mixing two or more thermally reactive reagents. Contacting 102 and/or preparing the non-flammable gas mixture may include contacting, selecting, formulating, and/or preparing a mixture of a combustion fuel and molecular oxygen, a mixture of a halocarbon and molecular oxygen, and/or other mixtures described herein with respect to the non-flammable gas mixture 30 (e.g., 2% ethylene in air, 1% chloroethane in air, 0.01% methyl bromide in air).

Applying 104 the energy discharge includes applying the energy discharge into, at, and/or to the test article to test whether the discharged energy generates an ignition source at the test article that is sufficient to react the non-flammable gas mixture in contact with the test article. Applying 104 the energy discharge may also be referred to as activating the test article, energizing the test article, and/or ignition hazard simulation. The energy discharge may simulate and/or may be actual operating conditions that the test article may experience such as a lightning strike, a static electrical charge discharge, heat, and/or a spark. Applying 104 the energy discharge may include applying a simulated lightning strike to the test article, applying a voltage across the test article (e.g., a voltage greater than 1 kV (kilovolts) or greater than 5 kV, and generally less than 100 kV), supplying an electrical current through the test article (e.g., a current greater than 1 A (amperes) or greater than 10 A, and generally less than 100,000 A). The energy discharge may have a peak power of greater than 1 kW (kilowatts) or greater than 10 kW, and generally less than 10,000 kW. The energy discharge may be relatively short, for example, having a duration of less than 1 second, less than 0.1 seconds, less than 0.01 seconds, or less than 0.001 seconds, and generally longer than 1 nanosecond. Applying 104 the energy discharge may include heating the test article (e.g., heating a region of the test article), for example, heating to a temperature greater than 100° C., greater than 200° C., or greater than 300° C., and generally less than 2,000° C.

Measuring 106 includes measuring the amount of the components of the non-flammable gas mixture that represents the amount of the thermally reactive reagent in the non-flammable gas mixture that reacted in response to applying 104 the energy discharge. The amount of the components of the non-flammable gas mixture may be a proxy of the amount of the thermally reactive reagent in the (potentially) reacted non-flammable gas mixture. Measuring 106 may include measuring an amount of the thermally reactive reagent and/or the oxidant remaining in the non-flammable gas mixture after applying 104 the energy discharge. Measuring 106 may include measuring an amount of the reaction product produced by thermal reaction (e.g., combustion and/or thermal decomposition) of the thermally reactive reagent after applying 104 the energy discharge. Because non-flammable gas mixture may include relatively little reaction product before applying 104 the energy discharge, measuring the amount of the reaction product may be subject to less error and/or have higher precision than measuring the amount of the thermally reactive reagent or the oxidant. Additionally or alternatively, the relative change of concentration (after applying 104 the energy discharge to before applying 104 the energy discharge) of the reaction product may be substantially greater than the corresponding relative change of concentration of the thermally reactive reagent or the oxidant.

Measuring 106 generally includes measuring the components of the non-flammable gas mixture with a high sensitivity technique, for example, a technique sensitive to low concentrations and/or small changes (e.g., concentrations and/or absolute changes of parts per million or parts per billion). Measuring 106 may include measuring by a gas analysis technique such as mass spectrometry, gas chromatography, or gas chromatography mass spectrometry. Measuring 106 may include measuring by an optical technique selected from the group consisting of optical spectrometry, optical absorbance, optical transmittance, optical reflectance, nephelometry, luminescence, fluorescence, phosphorescence, laser-induced fluorescence, planar laser-induced fluorescence, laser-excited atomic fluorescence, and Fourier transform infrared spectrometry.

Determining 108 incendivity may include determining the presence and/or absence of a thermal reaction in response to the energy discharge (e.g., combustion or thermal breakdown of the thermally reactive reagent 32). Determining 108 incendivity may include determining whether thermal reaction (combustion or thermal breakdown) occurred above a threshold level (e.g., combustion or breakdown products are present at a concentration greater than a threshold level). Determining 108 incendivity may include determining the presence and/or absence of an ignition source with greater than a threshold energy that was generated in response to the energy discharge. Determining 108 incendivity may include comparing a parameter related to the amount of thermally reactive reagent that reacted (e.g., the concentration of the thermally reactive reagent and/or the concentration of the reaction product) to a predefined threshold. The threshold levels of reaction and/or energy may be representative of an ignition source that would be an ignition hazard. Hence, determining 108 may include determining that the test article generated an ignition hazard in response to the energy discharge. Determining 108 may include determining a level of incendivity of the test article subject to the energy discharge based upon the amount of thermally reactive reagent that reacted (and/or a proxy thereof such as the concentration of the reaction product and/or the oxidant).

Methods 100 may include verifying 110 that the non-flammable gas mixture reacts to a thermal input by discharging a controlled ignition source (such as controlled ignition source 72) in the non-flammable gas mixture and after the controlled ignition source discharge, measuring the amount of one or more components (e.g., the indicator species) of the non-flammable gas mixture to verify that at least a portion of the thermally reactive reagent reacted in response to discharging the controlled ignition source. Verifying 110 may be performed before or after applying 104 the energy discharge and measuring 106 the components of the potentially reacted non-flammable gas mixture. Verifying 110 may be performed in the optional test chamber.

Verifying 110 with a reliable ignition source such as the controlled ignition source verifies that components of the corresponding test system (such as detection device 50) function properly. Additionally or alternatively, verifying 110 may provide a reference amount of thermally reactive reagent (or proxy such as concentration of the reaction product) that is generated in response to an ignition source (optionally an ignition source of predetermined energy).

Examples of inventive subject matter according to the present disclosure are described in the following enumerated paragraphs.

A1. An incendivity test method comprising:

contacting a test article with a non-flammable gas mixture that includes a thermally reactive reagent;

applying an energy discharge to the test article while the test article is in contact with the non-flammable gas mixture;

after applying the energy discharge, measuring an amount of one or more components of the non-flammable gas mixture that represents an amount of the thermally reactive reagent that reacted in response to applying the energy discharge; and determining an incendivity of the test article in response to the energy discharge based upon the amount of the thermally reactive reagent that reacted in response to applying the energy discharge.

A2. The method of paragraph A1, wherein the contacting the test article includes contacting the test article in a test chamber with the non-flammable gas mixture.

A2.1. The method of paragraph A2, wherein the contacting includes filling the test chamber with the non-flammable gas mixture, and optionally wherein the filling includes filing the test chamber with the non-flammable gas mixture to a pressure of at least one of greater than 50 kPa, greater than 70 kPa, greater than 90 kPa, greater than 100 kPa, less than 200 kPa, less than 150 kPa, less than 120 kPa, less than 100 kPa, about 70 kPa, and about 100 kPa.

A3. The method of any of paragraphs A1-A2.1, wherein the contacting includes contacting the test article with the non-flammable gas mixture at a pressure of at least one of greater than 50 kPa, greater than 70 kPa, greater than 90 kPa, greater than 100 kPa, less than 200 kPa, less than 150 kPa, less than 120 kPa, less than 100 kPa, about 70 kPa, and about 100 kPa.

A4. The method of any of paragraphs A1-A3, wherein the contacting includes immersing the test article in the non-flammable gas mixture, and optionally flowing a stream of the non-flammable gas mixture over the test article.

A5. The method of any of paragraphs A1-A4, wherein the thermally reactive reagent is configured to react in response to an ignition source to produce a reaction product.

A6. The method of any of paragraphs A1-A5, wherein the thermally reactive reagent includes, optionally is, at least one of a thermally reactive gas and a thermally reactive aerosol.

A7. The method of any of paragraphs A1-A6, wherein the non-flammable gas mixture is a mixture that is too lean to support self-propagating combustion of the thermally reactive reagent.

A8. The method of any of paragraphs A1-A7, wherein the non-flammable gas mixture has a concentration of the thermally reactive reagent that is below a lean ignition limit.

A9. The method of any of paragraphs A1-A8, wherein the thermally reactive reagent is at least one of gaseous and vaporous.

A10. The method of any of paragraphs A1-A9, wherein the non-flammable gas mixture includes an aerosol of the thermally reactive reagent.

A11. The method of any of paragraphs A1-A10, wherein the non-flammable gas mixture includes a plurality of thermally reactive reagents.

A11.1. The method of paragraph A11, wherein each of the thermally reactive reagents is configured to react in response to a different ignition source to produce a corresponding reaction product.

A12. The method of any of paragraphs A1-A11.1, wherein the thermally reactive reagent is a combustion fuel, optionally selected from the group consisting of a hydrocarbon fuel, a flammable gas, molecular hydrogen, methane, propane, gasoline, kerosene, and ethylene.

A13. The method of any of paragraphs A1-A12, wherein the thermally reactive reagent is configured to thermally decompose.

A14. The method of any of paragraphs A1-A13, wherein the thermally reactive reagent is a halocarbon, optionally selected from the group consisting of an alkyl halide, a chlorocarbon, a fluorocarbon, a bromocarbon, a chlorofluorocarbon, chloroethane, and methyl bromide.

A15. The method of any of paragraphs A1-A14, further comprising preparing the non-flammable gas mixture by mixing the thermally reactive reagent with one or more of an oxidant, a diluent, and another thermally reactive reagent.

A16. The method of any of paragraphs A1-A15, wherein the non-flammable gas mixture includes an oxidant.

A16.1. The method of paragraph A16, wherein the thermally reactive reagent is configured to react with the oxidant to produce a/the reaction product.

A16.2. The method of any of paragraphs A16-A16.1, wherein the non-flammable gas mixture includes a plurality of thermally reactive reagents and each of the thermally reactive reagents is configured to react with the oxidant in response to a different ignition source to produce a corresponding reaction product.

A16.3. The method of any of paragraphs A16-A16.2, wherein the non-flammable gas mixture includes a plurality of thermally reactive reagents and wherein the non-flammable gas mixture includes a plurality of corresponding oxidants wherein each corresponding oxidant is configured to react with at least one of the thermally reactive reagents to produce a/the corresponding reaction product.

A16.4. The method of any of paragraphs A16-A16.3, wherein the oxidant is at least one of gaseous and vaporous.

A16.5. The method of any of paragraphs A16-A16.4, wherein the non-flammable gas mixture includes an aerosol of the oxidant.

A16.6. The method of any of paragraphs A16-A16.5, where the oxidant includes one or more species selected from the group consisting of molecular oxygen, nitrous oxide, and hydrogen peroxide.

A17. The method of any of paragraphs A1-A16.6, wherein the non-flammable gas mixture includes a diluent.

A17.1. The method of paragraph A17, wherein the diluent is configured not to react with the thermally reactive reagent.

A17.2. The method of any of paragraphs A17-A17.1, wherein the diluent includes one or more species selected from the group consisting of an inert gas, nitrogen, argon, and helium.

A18. The method of any of paragraphs A1-A17.2, wherein a/the reaction product is selected from the group consisting of water, carbon dioxide, carbon monoxide, formaldehyde, hydrochloric acid, hydrofluoric acid, hydrobromic acid, carbonyl difluoride, carbonyl dichloride, carbonyl dibromide, molecular fluorine, molecular chlorine, and molecular bromine.

A19. The method of any of paragraphs A1-A18, wherein the non-flammable gas mixture includes a volume fraction of chloroethane of about 1% in air.

A20. The method of any of paragraphs A1-A19, wherein the non-flammable gas mixture includes a volume fraction of methyl bromide of about 0.01% in air.

A21. The method of any of paragraphs A1-A20, wherein the non-flammable gas mixture includes a volume fraction of ethylene of less than 2.7%, less than 2.5%, about 2%, and/or greater than 0.1% in air.

A22. The method of any of paragraphs A1-A21, wherein the applying the energy discharge includes applying a simulated lightning strike to the test article.

A23. The method of any of paragraphs A1-A22, wherein the applying the energy discharge includes 1 generating an arc at the test article.

A24. The method of any of paragraphs A1-A23, wherein the applying the energy discharge includes applying a voltage across the test article, and optionally wherein the voltage is greater than 1 kV or greater than 5 kV.

A25. The method of any of paragraphs A1-A24, wherein the applying the energy discharge includes supplying a current through the test article, and optionally wherein the current is greater than 1 A or greater than 10 A.

A26. The method of any of paragraphs A1-A25, wherein the energy discharge has a peak power of greater than 1 kW or greater than 10 kW.

A27. The method of any of paragraphs A1-A26, wherein the applying the energy discharge includes heating the test article.

A28. The method of any of paragraphs A1-A27, wherein the applying the energy discharge generates an ignition source at the test article sufficient to react the thermally reactive reagent to produce a/the reaction product.

A29. The method of any of paragraphs A1-A28, wherein the measuring includes measuring an amount of the thermally reactive reagent remaining in the non-flammable gas mixture after applying the energy discharge.

A30. The method of any of paragraphs A1-A29, wherein the measuring includes measuring an amount of an/the oxidant remaining in the non-flammable gas mixture after applying the energy discharge.

A31. The method of any of paragraphs A1-A30, wherein the measuring includes measuring an amount of a/the reaction product produced by thermal reaction of the thermally reactive reagent after applying the energy discharge.

A32. The method of any of paragraphs A1-A31, wherein the measuring includes measuring by a gas analysis technique selected from the group consisting of mass spectrometry, gas chromatography, and gas chromatography mass spectrometry.

A33. The method of any of paragraphs A1-A32, wherein the measuring includes measuring by an optical technique selected from the group consisting of optical spectrometry, optical absorbance, optical transmittance, optical reflectance, nephelometry, luminescence, fluorescence, phosphorescence, laser-induced fluorescence, planar laser-induced fluorescence, laser-excited atomic fluorescence, and Fourier transform infrared spectrometry.

A34. The method of any of paragraphs A1-A33, wherein the determining the incendivity includes comparing a parameter related to the amount of thermally reactive reagent that reacted to a predefined threshold.

A35. The method of any of paragraphs A1-A34, wherein the determining the incendivity includes determining that the test article generated an ignition hazard in response to the energy discharge based upon whether the amount of thermally reactive reagent that reacted is greater than the predefined threshold.

A36. The method of any of paragraphs A1-A35, wherein the determining the incendivity includes determining a level of incendivity based upon the amount of thermally reactive reagent that reacted.

A37. The method of any of paragraphs A1-A36, further comprising verifying the non-flammable gas mixture reacts to a thermal input by discharging a controlled ignition source in the non-flammable gas mixture and, after the controlled ignition source discharge, measuring the amount of one or more components of the non-flammable gas mixture to verify that at least a portion of the thermally reactive reagent reacted in response to discharging the controlled ignition source.

A37.1. The method of paragraph A37, wherein the verifying is performed after the determining.

A37.2. The method of any of paragraphs A37-A37.1, wherein the controlled ignition source is discharged within a/the test chamber with the test article.

A37.3. The method of any of paragraphs A37-A37.2, wherein the discharging the controlled ignition source discharges an energy of less than 1,000 µJ, less than 500 µJ, less than 200 µJ, less than 100 µJ, greater than 10 µJ, greater than 50 µJ, greater than 100 µJ, greater than 200 µJ, and/or about 200 µJ.

A37.4. The method of any of paragraphs A37-A37.3, wherein the controlled ignition source produces, optionally is, at least one of an electrical arc, a spark, a hot surface, a hot particle ejection, an electrostatic discharge, and a flame.

A38. The method of any of paragraphs A1-A37.4, wherein the test article is a solid form and optionally includes one or more of metal, aluminum, plastic, and fiber-reinforced composite material.

A39. The method of any of paragraphs A1-A38, wherein the test article is an aerospace component, and optionally at least one of an aircraft skin, an aircraft frame, a wing, a fuel handling component, a fuel system, a fuel tank, a fuel pump, and an electrical enclosure.

B1. An incendivity test system, optionally an aerospace component incendivity test system, comprising:
a test chamber;
a non-flammable gas mixture in the test chamber, wherein the non-flammable gas mixture includes a thermally reactive reagent that is formulated to thermally react to produce a reaction product;
a test article in the test chamber in contact with the non-flammable gas mixture;
an energy source configured to apply an energy discharge to the test article; and
a detection device configured to measure an amount of one or more indicator species selected from the group consisting of a component of the non-flammable gas mixture and the reaction product.

B2. The system of paragraph B1, wherein the thermally reactive reagent includes, optionally is, at least one of a thermally reactive gas and a thermally reactive aerosol.

B3. The system of any of paragraphs B1-B2, wherein the non-flammable gas mixture is a mixture that is too lean to support self-propagating combustion of the thermally reactive reagent.

B4. The system of any of paragraphs B1-B3, wherein the non-flammable gas mixture has a concentration of the thermally reactive reagent that is below a lean ignition limit.

B5. The system of any of paragraphs B1-B4, wherein the thermally reactive reagent is at least one of gaseous and vaporous.

B6. The system of any of paragraphs B1-B5, wherein the non-flammable gas mixture includes an aerosol of the thermally reactive reagent.

B7. The system of any of paragraphs B1-B6, wherein the thermally reactive reagent is a combustion fuel, optionally selected from the group consisting of a hydrocarbon fuel, a flammable gas, molecular hydrogen, methane, propane, gasoline, kerosene, and ethylene.

B8. The system of any of paragraphs B1-B7, wherein the thermally reactive reagent is configured to thermally decompose.

B9. The system of any of paragraphs B1-B8, wherein the thermally reactive reagent is a halocarbon, optionally selected from the group consisting of an alkyl halide, a chlorocarbon, a fluorocarbon, a bromocarbon, a chlorofluorocarbon, chloroethane, and methyl bromide.

B10. The system of any of paragraphs B1-B9, wherein the non-flammable gas mixture includes a plurality of thermally reactive reagents.

B10.1. The system of paragraph B10, wherein each of the thermally reactive reagents is configured to react in response to a different ignition source to produce a corresponding reaction product.

B11. The system of any of paragraphs B1-B10.1, wherein the non-flammable gas mixture includes an oxidant.

B11.1. The system of paragraph B11, wherein the thermally reactive reagent is configured to react with the oxidant to produce the reaction product.

B11.2. The system of any of paragraphs B11-B11.1, wherein the non-flammable gas mixture includes a plurality of thermally reactive reagents and each of the thermally reactive reagents is configured to react with the oxidant in response to a different ignition source to produce a corresponding reaction product.

B11.3. The system of any of paragraphs B11-B11.2, wherein the non-flammable gas mixture includes a plurality of thermally reactive reagents and wherein the non-flammable gas mixture includes a plurality of corresponding oxidants wherein each corresponding oxidant is configured to react with at least one of the thermally reactive reagents to produce a/the corresponding reaction product.

B11.4. The system of any of paragraphs B11-B11.3, wherein the oxidant is at least one of gaseous and vaporous.

B11.5. The system of any of paragraphs B11-B11.4, wherein the non-flammable gas mixture includes an aerosol of the oxidant.

B11.6. The system of any of paragraphs B11-B11.5, where the oxidant includes one or more species selected from the group consisting of molecular oxygen, nitrous oxide, and hydrogen peroxide.

B12. The system of any of paragraphs B1-B11.6, wherein the non-flammable gas mixture includes a diluent.

B12.1. The system of paragraph B12, wherein the diluent is configured not to react with the thermally reactive reagent.

B12.2. The system of any of paragraphs B12-B12.1, wherein the diluent includes one or more species selected from the group consisting of an inert gas, nitrogen, argon, and helium.

B13. The system of any of paragraphs B1-B12.2, wherein the reaction product is selected from the group consisting of water, carbon dioxide, carbon monoxide, formaldehyde, hydrochloric acid, hydrofluoric acid, hydrobromic acid, carbonyl difluoride, carbonyl dichloride, carbonyl dibromide, molecular fluorine, molecular chlorine, and molecular bromine.

B14. The system of any of paragraphs B1-B13, wherein the non-flammable gas mixture includes a volume fraction of chloroethane of about 1% in air.

B15. The system of any of paragraphs B1-B14, wherein the non-flammable gas mixture includes a volume fraction of methyl bromide of about 0.01% in air.

B16. The system of any of paragraphs B1-B15, wherein the non-flammable gas mixture includes a volume fraction of ethylene of less than 2.7%, less than 2.5%, about 2%, and/or greater than 0.1% in air.

B17. The system of any of paragraphs B1-B16, wherein the detection device is a gas sampling device, optionally selected from the group consisting of a mass spectrometer, a gas chromatograph, and a gas chromatography mass spectrometer.

B18. The system of any of paragraphs B1-B17, wherein the detection device is an optional detection device, optionally selected from the group consisting of an optical spectrometer, a fluorescence spectrometer, a laser-induced fluorescence apparatus, a planar laser-induced fluorescence apparatus, a laser-excited atomic fluorescence apparatus, and a Fourier transform infrared spectrometer.

B19. The system of any of paragraphs B1-B18, wherein the energy source is at least one of a lightning strike simulator, an electrical power source, an electrical voltage source, and an electrical current source.

B20. The system of any of paragraphs B1-B19, further comprising a controller configured to discharge the energy source to apply the energy discharge to the test article, configured to measure the presence and/or amount of the indicator species, and configured to determine an incendivity of the test article in response to the energy discharge based upon the presence and/or amount of the indicator species.

B20.1. The system of paragraph B20, wherein the controller is programmed to perform the incendivity test method of any of paragraphs A1-A39.

B21. The system of any of paragraphs B1-B20.1, further comprising a gas source configured to supply the non-flammable gas mixture to the test chamber and optionally wherein the gas source is connected to the test chamber via a gas inlet port of the test chamber and a valve that is configured to control a flow of the non-flammable gas mixture from the gas source to the test chamber.

B22. The system of any of paragraphs B1-B21, wherein the test article is a solid form and optionally includes one or more of metal, aluminum, plastic, and fiber-reinforced composite material.

B23. The system of any of paragraphs B1-B22, wherein the test article is an aerospace component, and optionally at least one of an aircraft skin, an aircraft frame, a wing, a fuel handling component, a fuel system, a fuel tank, a fuel pump, and an electrical enclosure.

B24. The use of the incendivity test system of any of paragraphs B1-B23 to test the incendivity of the test article in response to the energy discharge.

C1. The use of a non-flammable gas mixture to test the incendivity of a test article, optionally by applying an energy discharge to the test article while the test article is in contact with the non-flammable gas mixture and measuring an amount of one or more components of the non-flammable gas mixture after applying the energy discharge to determine the incendivity based upon the amount of the one or more components of the non-flammable gas mixture that is measured.

C2. The use of paragraph C1, wherein the non-flammable gas mixture and/or the test article are as recited in any of paragraphs A1-A39 and/or B1-B23.

As used herein, the terms "adapted" and "configured" mean that the element, component, or other subject matter is designed and/or intended to perform a given function. Thus, the use of the terms "adapted" and "configured" should not be construed to mean that a given element, component, or other subject matter is simply "capable of" performing a given function but that the element, component, and/or other subject matter is specifically selected, created, prepared, formed, implemented, utilized, programmed, and/or designed for the purpose of performing the function. It is also within the scope of the present disclosure that elements, components, and/or other recited subject matter that is recited as being adapted to perform a particular function may additionally or alternatively be described as being configured to perform that function, and vice versa. Similarly, subject matter that is recited as being configured to perform a particular function may additionally or alternatively be described as being operative to perform that function.

As used herein, the phrase, "for example," the phrase, "as an example," and/or simply the term "example," when used with reference to one or more components, features, details, structures, embodiments, and/or methods according to the present disclosure, are intended to convey that the described component, feature, detail, structure, embodiment, and/or method is an illustrative, non-exclusive example of components, features, details, structures, embodiments, and/or methods according to the present disclosure. Thus, the described component, feature, detail, structure, embodiment, and/or method is not intended to be limiting, required, or exclusive/exhaustive; and other components, features, details, structures, embodiments, and/or methods, including structurally and/or functionally similar and/or equivalent components, features, details, structures, embodiments, and/or methods, are also within the scope of the present disclosure.

As used herein, the phrases "at least one of" and "one or more of," in reference to a list of more than one entity, means any one or more of the entities in the list of entities, and is not limited to at least one of each and every entity specifically listed within the list of entities. For example, "at least one of A and B" (or, equivalently, "at least one of A or B," or, equivalently, "at least one of A and/or B") may refer to A alone, B alone, or the combination of A and B.

As used herein, the singular forms "a", "an" and "the" may be intended to include the plural forms as well, unless the context clearly indicates otherwise.

The various disclosed elements of systems and steps of methods disclosed herein are not required of all systems and methods according to the present disclosure, and the present disclosure includes all novel and non-obvious combinations and subcombinations of the various elements and steps disclosed herein. Moreover, any of the various elements and steps, or any combination of the various elements and/or steps, disclosed herein may define independent inventive subject matter that is separate and apart from the whole of a disclosed system or method. Accordingly, such inventive subject matter is not required to be associated with the specific systems and methods that are expressly disclosed herein, and such inventive subject matter may find utility in systems and/or methods that are not expressly disclosed herein.

The invention claimed is:

1. An incendivity test method comprising:
  contacting a test article with a non-flammable gas mixture, wherein the non-flammable gas mixture includes a thermally reactive reagent;
  applying an energy discharge to the test article while the test article is in contact with the non-flammable gas mixture;
  after applying the energy discharge, measuring an amount of one or more components of the non-flammable gas mixture that represents an amount of the thermally reactive reagent that reacted in response to applying the energy discharge; and
  determining an incendivity of the test article in response to the energy discharge based upon the amount of the thermally reactive reagent that reacted in response to applying the energy discharge.

2. The method of claim 1, wherein the non-flammable gas mixture is a mixture that is too lean to support self-propagating combustion of the thermally reactive reagent.

3. The method of claim 1, wherein the applying the energy discharge includes applying a simulated lightning strike to the test article.

4. The method of claim 1, wherein the energy discharge has a peak power of greater than 1 kW (kilowatt).

5. The method of claim 1, wherein the measuring includes measuring an amount of a reaction product produced by thermal reaction of the thermally reactive reagent after applying the energy discharge.

6. The method of claim 1, wherein the measuring includes measuring by a gas analysis technique selected from the group consisting of mass spectrometry, gas chromatography, and gas chromatography mass spectrometry.

7. The method of claim 1, wherein the measuring includes measuring by an optical technique selected from the group consisting of optical spectrometry, optical absorbance, optical transmittance, optical reflectance, nephelometry, luminescence, fluorescence, phosphorescence, laser induced fluorescence, planar laser induced fluorescence, laser excited atomic fluorescence, and Fourier transform infrared spectrometry.

8. The method of claim 1, wherein the non-flammable gas mixture includes a plurality of thermally reactive reagents, wherein each of the thermally reactive reagents is configured to react in response to a different ignition source to produce a corresponding reaction product.

9. The method of claim 1, wherein the thermally reactive reagent is a combustion fuel.

10. The method of claim 1, wherein the thermally reactive reagent is configured to thermally decompose.

11. The method of claim 1, wherein the thermally reactive reagent is a halocarbon.

12. The method of claim 1, wherein the contacting includes immersing the test article in the non-flammable gas mixture.

13. The method of claim 1, wherein the contacting includes flowing a stream of the non-flammable gas mixture over the test article.

14. The method of claim 13, wherein the flowing includes recirculating the non-flammable gas mixture over the test article.

15. The method of claim 1, further comprising preparing the non-flammable gas mixture by mixing the thermally reactive reagent with one or more of an oxidant, a diluent, and another thermally reactive reagent.

16. The method of claim 1, wherein the contacting includes contacting the test article with the non-flammable gas mixture at a pressure of at least 50 kPa.

17. The method of claim 1, wherein the thermally reactive reagent includes at least one of a thermally reactive gas and a thermally reactive aerosol.

18. The method of claim 1, wherein the non-flammable gas mixture includes an aerosol of the thermally reactive reagent.

19. The method of claim 1, wherein the non-flammable gas mixture includes an oxidant, and wherein the non-flammable gas mixture includes a plurality of thermally reactive reagents and each of the thermally reactive reagents is configured to react with the oxidant in response to a different ignition source to produce a corresponding reaction product.

20. The method of claim 1, wherein the non-flammable gas mixture includes a plurality of thermally reactive reagents, and wherein the non-flammable gas mixture includes a plurality of corresponding oxidants wherein each corresponding oxidant is configured to react with at least one of the thermally reactive reagents to produce a corresponding reaction product.

21. The method of claim 1, wherein the determining the incendivity includes comparing a parameter related to the amount of thermally reactive reagent that reacted to a predefined threshold.

22. The method of claim 1, wherein the determining the incendivity includes determining that the test article generated an ignition hazard in response to the energy discharge based upon whether the amount of thermally reactive reagent that reacted is greater than a predefined threshold.

23. The method of claim 1, wherein the determining the incendivity includes determining a level of incendivity based upon the amount of thermally reactive reagent that reacted.

24. The method of claim 1, further comprising, before or after the applying the energy discharge and the measuring the amount of one or more component, verifying the non-flammable gas mixture reacts to a thermal input by discharging a controlled ignition source in the non-flammable gas mixture and, after the controlled ignition source discharge, measuring the amount of one or more components of the non-flammable gas mixture to verify that at least a portion of the thermally reactive reagent reacted in response to discharging the controlled ignition source.

25. The method of claim 24, wherein the verifying is performed after the determining the incendivity of the test article.

26. The method of claim 1, wherein the test article is at least one of an aircraft skin, an aircraft frame, an aircraft wing, a fuel handling component, a fuel system, a fuel tank, a fuel pump, and an electrical enclosure.

27. An incendivity test system comprising:
- a non-flammable gas mixture, wherein the non-flammable gas mixture includes a thermally reactive reagent that is formulated to thermally react to produce a reaction product;
- a test article in contact with the non-flammable gas mixture;
- an energy source configured to apply an energy discharge to the test article; and
- a detection device configured to measure an amount of one or more indicator species selected from the group consisting of a component of the non-flammable gas mixture and the reaction product.

\* \* \* \* \*